(12) United States Patent
Mazur (10) Patent No.: US 8,581,709 B2
(45) Date of Patent: Nov. 12, 2013

(54) MODULAR PILLBOX SYSTEM

(76) Inventor: Robert G. Mazur, Canton, MI (US)

( * ) Notice: Subject to any disclaimer, the term of this patent is extended or adjusted under 35 U.S.C. 154(b) by 281 days.

(21) Appl. No.: 13/205,199

(22) Filed: Aug. 8, 2011

(65) Prior Publication Data

US 2012/0006708 A1   Jan. 12, 2012

Related U.S. Application Data (63) Continuation-in-part of application No. 12/117,978, filed on May 9, 2008, now abandoned.

(60) Provisional application No. 60/928,370, filed on May 9, 2007, provisional application No. 61/065,612, filed on Feb. 3, 2008.

(51) Int. Cl.
  *G08B 1/00* (2006.01)
  *G04B 47/00* (2006.01)
  *B65D 83/04* (2006.01)

(52) U.S. Cl.
  USPC ........... 340/309.16; 340/309.7; 340/691.1; 340/692; 368/1; 368/10; 221/2; 222/23; 206/528; 206/534; 206/538

(58) Field of Classification Search
  USPC ..................... 340/309.16; 206/534
  See application file for complete search history.

(56) References Cited

U.S. PATENT DOCUMENTS

| | | | |
|---|---|---|---|
| 4,223,801 A | 9/1980 | Carlson | |
| 4,275,384 A | 6/1981 | Hicks et al. | |
| 4,473,884 A | 9/1984 | Behl | |
| 5,200,891 A | 4/1993 | Kehr et al. | |
| 5,408,443 A | 4/1995 | Weinberger | |
| 5,642,731 A | 7/1997 | Kehr | |
| 5,752,235 A | 5/1998 | Kehr et al. | |
| 5,838,224 A | 11/1998 | Andrews | |
| 5,850,937 A | 12/1998 | Rauche | |
| 5,954,225 A | 9/1999 | Powe | |
| 6,032,085 A | 2/2000 | Laurent et al. | |
| 6,119,892 A | 9/2000 | Laurent et al. | |
| 6,259,654 B1 | 7/2001 | de la Huerga | |
| 6,263,259 B1 | 7/2001 | Bartur | |
| 6,294,999 B1 | 9/2001 | Yarin et al. | |
| 6,301,196 B1 | 10/2001 | Daniel | |

(Continued)

FOREIGN PATENT DOCUMENTS

WO   WO 2004073498 A2   9/2004

*Primary Examiner* — Donnie Crosland
(74) *Attorney, Agent, or Firm* — Brinks Gilson & Lione (57) ABSTRACT

A modular pillbox that includes a base unit and a plurality of modules that can be interchangeably coupled to the base unit. The base unit includes a plurality of interior compartments defined by a top, a bottom and at least one side wall, openable doors that close the tops of the plurality of interior compartments, one-way passages in one of the bottoms or the at least one side wall of each interior compartment through which pills can be pushed into the interior compartments, and an opening in a front portion of the base unit. The plurality of modules includes a cover plate that couples to the base unit and covers the opening, and various electronic packages that removable couple to the base unit and cover the opening. An interactive electronic pillbox that includes the platform or base unit and an electronics package includes data entry, data display, data transmitting and data processing functions which allow for interactive healthcare management by individuals and healthcare personnel directly or remotely. Form a remote location a healthcare provider can monitor, manage, evaluate and maintain a periodic record of the healthcare of a user of the electronic interactive pillbox.

20 Claims, 10 Drawing Sheets

(56) References Cited

U.S. PATENT DOCUMENTS

| | | |
|---|---|---|
| 6,449,218 B1 | 9/2002 | Lluch |
| 6,625,518 B2 | 9/2003 | Depeursinge |
| 6,662,081 B1 | 12/2003 | Jacober et al. |
| 7,158,011 B2 | 1/2007 | Brue |
| 7,602,275 B2 | 10/2009 | Dishongh et al. |
| 2001/0022758 A1 | 9/2001 | Howard |
| 2001/0032098 A1 | 10/2001 | Kulkarni |
| 2002/0067270 A1 | 6/2002 | Yarin et al. |
| 2004/0179430 A1 | 9/2004 | Bahar et al. |
| 2006/0022806 A1 | 2/2006 | Auerbach |

MODULAR PILLBOX SYSTEM

RELATED APPLICATIONS

The present application is a continuation-in-part of U.S. patent application Ser. No. 12/117,978, filed May 9, 2008 now abandoned which is based upon U.S. Provisional Application No. 60/928,370, filed May 9, 2007 and U.S. Provisional Application No. 61/065,612, filed Feb. 13, 2008, to each of which priority is claimed under 35 U.S.C. §120 and of which the complete disclosures are hereby expressly incorporated by reference.

TECHNICAL FIELD

The present invention relates to pillboxes for storing and organizing various medications, vitamins, supplements, etc. In particular, the present invention relates to an electronic interactive pillbox system that, in addition to storing and organizing various medications, vitamins, supplements, etc., provides advanced electronic features such as data management, interactive functions, symptom monitoring and medical healthcare journaling, etc.

BACKGROUND ART

Managing the medication taking process can be frustrating and confusing. Doctors prescribe multiple medications for different health conditions. Some medications might be taken daily, others twice a day, and yet others 3-4 times a day. When multiple medications are prescribed and each is to be taken at different intervals it can become difficult to remember when each medication is to be taken and thus there is a need for a simple management system for managing pill-taking, tacking medical patterns and maintaining a computerized interactive medical healthcare journal.

DISCLOSURE OF THE INVENTION

According to various features, characteristics and embodiments of the present invention which will become apparent as the description thereof proceeds, the present invention provides a modular pillbox which comprises a base unit and a plurality of modules that can be interchangeably coupled to the base unit,
 the base unit comprises:
  a plurality of interior compartments defined by a top, a bottom and at least one side wall;
  openable doors that close the tops of the plurality of interior compartments;
  one-way passages in one of the bottoms or the at least one side wall of each interior compartment through which pills can be pushed into the interior compartments; and
  an opening in a front portion of the base unit,
 the plurality of modules comprise:
  a cover plate that couples to the base unit and covers the opening; and
  an electronic package that couples to the base unit and covers the opening.

The present invention further provides an electronic interactive pillbox which comprises a base unit and a replaceable electronics module that can be removable coupled to the base unit,
 the base unit comprises:
  a plurality of interior compartments defined by a top, a bottom and at least one side wall;
  openable doors that close the tops of the plurality of interior compartments;
  one-way passages in one of the bottoms or the at least one side wall of each interior compartment through which pills can be pushed into the interior compartments; and
  an opening in a front portion of the base unit,
 the electronics module comprises:
  an electronic package that removably couples to the base unit within the opening so that close the opening and define a front face of the resulting electronic interactive pillbox,
 the electronic package coupling the electronic interactive pillbox to a remote terminal at which a healthcare provider can monitor, manage, evaluate and maintain a periodic record of the healthcare of a user of the electronic interactive pillbox.

BRIEF DESCRIPTION OF DRAWINGS

The present invention will be described with reference to the attached drawings which are given as non-limiting examples only, in which.

BEST MODE FOR CARRYING OUT THE INVENTION

The present invention is directed to an electronic interactive pillbox system that, in addition to storing and organizing various medications, vitamins, supplements, etc., provides advanced electronic features such as data management, interactive functions, etc. The present invention allows for a person to take an active role in their health management. For example, the present invention allows an individual to record multiple questions, and while talking to a physician, nurse or other healthcare worker, simultaneously play the questions and record answers given by the physician, nurse or other healthcare worker.

Through electronic circuitry, the questions and answers to and from the physician can be stored in an electronic data file. The electronic data file can be in any convenient format. With the recorded data file, the individual can take the electronic pillbox of the present invention back to their home and through a data transfer device such as a computer interface, docking port, USB connection, wireless link, etc. the data file can be downloaded to a computer or other mobile device for recording and storage of that meeting with the physician, nurse or other healthcare worker.

The data transfer device can also allow the electronic pillbox to function as an electronic monitoring device. Through the use of LED's and sensors, a person can know what medication to take, when to take the medication, and if they took or missed taking a medication. In this regard, sensors will monitor if the cover of a compartment of the electronic pillbox has been opened so that the contents of the compartment has been accessed. In addition LED's or other display devices will alert a user that it is time to take his/her medication and which medication to take. The use of different colored LED's will allow a user to know which medication to take and if they did not take the medication. For those who are color blind, the LED's could flash and/or the device can be provided with a speaker that can alert the person that it is time to take a medication or that the medication has not been taken.

A speaker and microphone provided on the electronic pillboxes of the present invention could also be used to record a personal message. For example, a caregiver or loved one can leave a voice prompt to take a medication together with words of comfort or encouragement.

The present invention incorporates a notepad, electronic display or message board to display the medications that a person is taking, as well as the dosages and frequencies. In addition, the display can display emergency contact information, whether or not a living will has been affected and the contact information of the administrator of any such living will. In addition to an onboard memory, the data transfer device can be used to transfer such information to a computer and/or transfer such information to a remote monitor, computer, data bank, etc. Further, security features can be incorporated, such as password clearance to allow caregivers, healthcare professionals, etc. to access and monitor such date and intervene with a patient's healthcare management when necessary.

According to one embodiment a scanner can be included on the electronic pillboxes of the present invention and used to scan information provided on the labels on medication containers. The scanned information can be used to assist in programming the electronic pillboxes. The scanned information can also be used to provide a stored or recorded audible directive related to the information.

Figure 1:
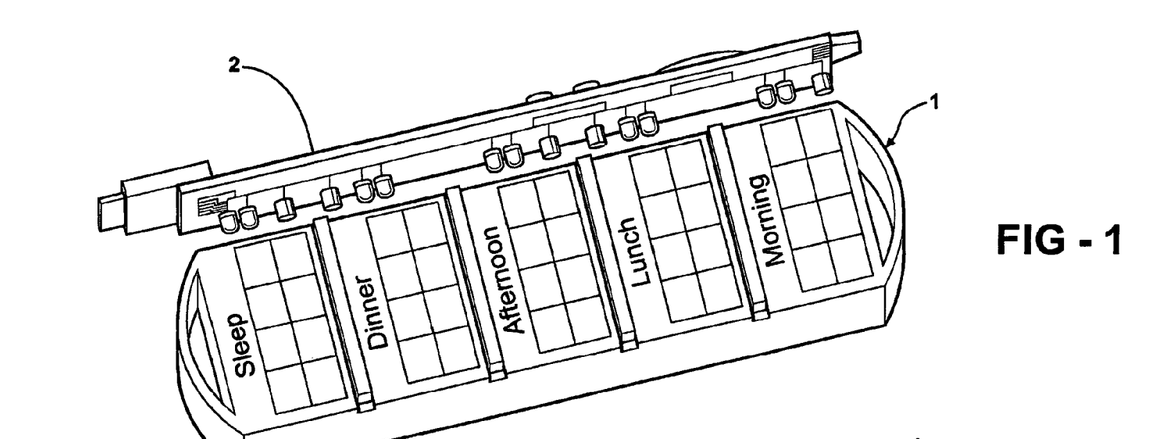
FIG. 1 is an exploded perspective view of an electronic pillbox according to one embodiment of the present invention.

FIG. 1 is an exploded perspective view of an electronic pillbox according to one embodiment of the present invention. The electronic pillbox of the present invention includes a multi-compartment pillbox 1 and a circuit board 2 that are coupled together. The pillbox 1 is of a multi-compartment style in which each compartment has a separate or individual cover. In general such pillbox structures are conventional. According to one embodiment, the pillbox 1 used for the present invention is disclosed in co-pending application Ser. No. 12/033,332, the complete disclosure of which is hereby expressly incorporated by reference. The pillbox 1 can include indicium that identifies individual compartments as shown and can be made from any suitable material such as plastic materials, resin materials, metals, etc.

The circuit board 2 has a number of conventional components some of which will be discussed in detail as the description of the present invention proceeds. Some of the conventional components include a programmable processor which, as discussed below, will allow the electronic pillbox to perform a number of functions related to managing an individual's medication schedule, including allowing monitoring or overseeing an individual's healthcare management by third parties.

The circuit board 2 can be formed separately and coupled to the pillbox 1 in any suitable fashion. According to alternative embodiments, some or all the components of the circuit board 2 can be formed directly into the pillbox 1 including printed circuit board components that can be printed or laminated or otherwise formed on or incorporated into the pillbox 1.

Figure 2:
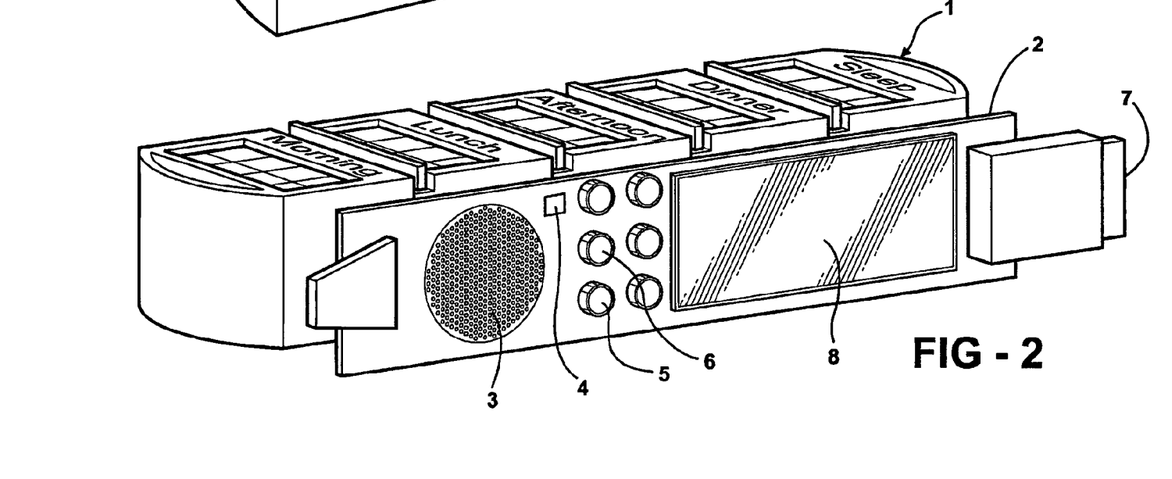
FIG. 2 is side perspective view of the electronic pillbox of FIG. 1.

FIG. 2 is side perspective view of the electronic pillbox of FIG. 1. The circuit board 2 shown in FIG. 2 includes a speaker 3 coupled to a recording device, chip, or circuit, a microphone 4 and one or more "record" and "play back" buttons 5 and 6. The combination of the speaker 3, recording device, chip, or circuit, microphone 4 and "record" and "play back" buttons 5 and 6, allow a user to pre-record questions that he/she might want to ask a healthcare worker, such as for example "is this rash a cancer?" In addition, the combination will allow a user to record answers and comments a healthcare worker will provide during a consultation. The use of multiple "record" and "play back" buttons 5 and 6 can be used for separate questions some or all of which can be programmed into the recording device, chip, or circuit. The configuration and number of the "record" and "play back" buttons 5 and 6 can vary from that shown without departing from the scope of the present invention.

A data transfer device is provided on the circuit board to allow information to be transferred between the electronic pillbox and other devices such as a computer, mobile devices, including cell phones, pagers, interactive testing device, etc. The date transfer device can be a USB connector 7 as shown, an antenna for wireless data transfer, a connector port that receives a transfer cable, a computer interface or docking port, etc.

A display 8 is provided on the circuit board 2 which can be use to display various information such as, but not limited to, medication information, pictures or photographs, emergency contact information, text messages or messages from loved ones. The display 8 could be as simple as a writable or re-writable paper or plastic surface or an electric or digital display that can display images, including textual images or graphic images, including photographs. In the case of an electric or digital display the image data could be stored in an onboard memory in the circuit board 2 and/or uploaded or updated by data transfer via the data transfer device.

Figure 3:
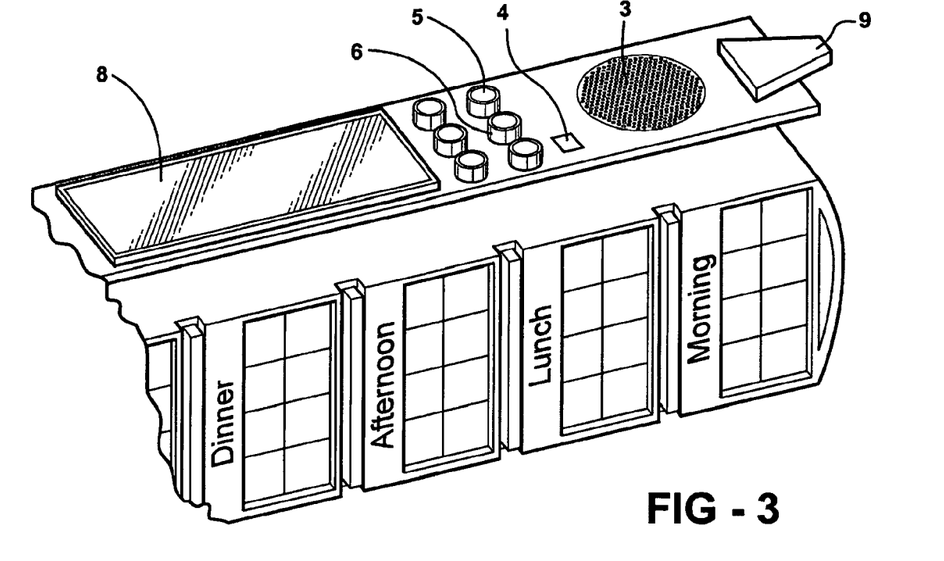
FIG. 3 is a side perspective view of one end of an electronic pillbox according to one embodiment of the present invention.

FIG. 3 is a side perspective view of one end of an electronic pillbox according to one embodiment of the present invention. One end of the circuit board 2 can be provided with a data scanning device 9 that can scan text, graphics, barcodes, etc. As one non-limiting example, the scanning device 9 could be used to scan information from a medicine container and store and/or display this information or a variation of this information on the display 8 and/or transfer this information via the data transfer device to another device, including a computer, other mobile devices, including cell phones, pagers, interactive testing devices, etc.

Figure 4:
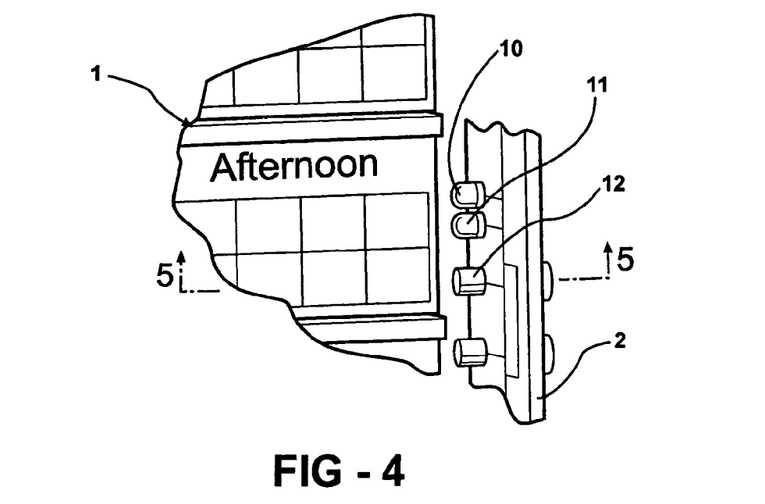
FIG. 4 is an enlarged exploded perspective view of an electronic pillbox according to one embodiment of the present invention.

FIG. 4 is an enlarged exploded perspective view of an electronic pillbox according to one embodiment of the present invention. As shown in FIG. 4 (and FIG. 1), the circuit board 1 includes a one or more LED's 10 and 11 and a sensor 12 which are positioned adjacent each of the compartments of the pillbox 1. In the illustrated embodiment, LED 10 produces a red light source and can be used to indicate that it is not time to take a medication contained in an adjacent compartment and LED 11 produces a green light source and can be use to indicate that it is time to take a medication contained in an adjacent compartment. The sensor 12, as discussed below is used to sense when a cover of an adjacent compartment has been opened. It will be understood from the following description that various types of sensors can be used for this purpose, including proximity sensors, optical sensors, magnetic sensors, etc.

Figure 5:
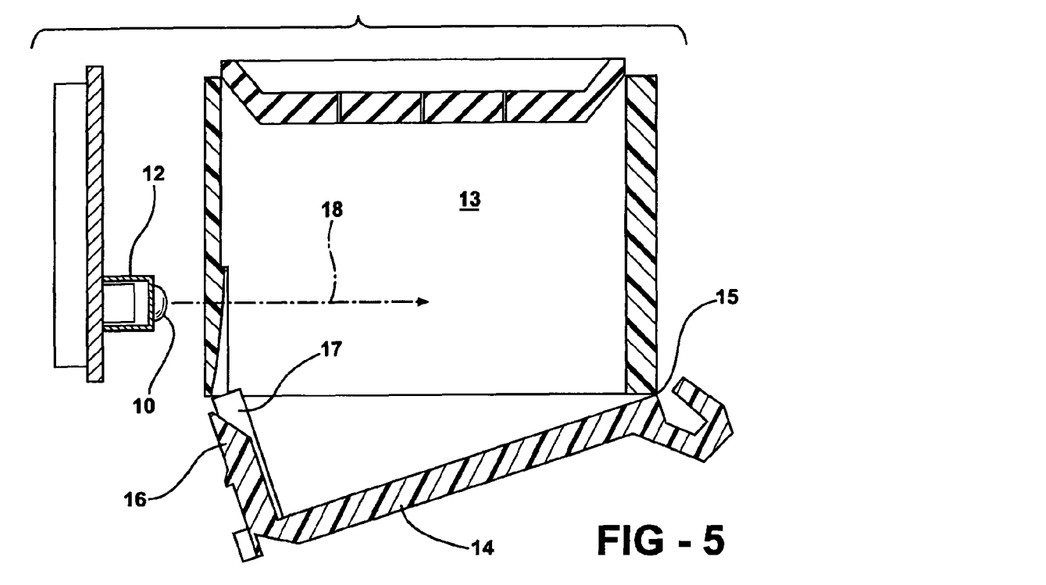
FIG. 5 is cross-sectional view of the electronic pillbox of FIG. 4 taken along sectional lines 5-5.
Figure 6:
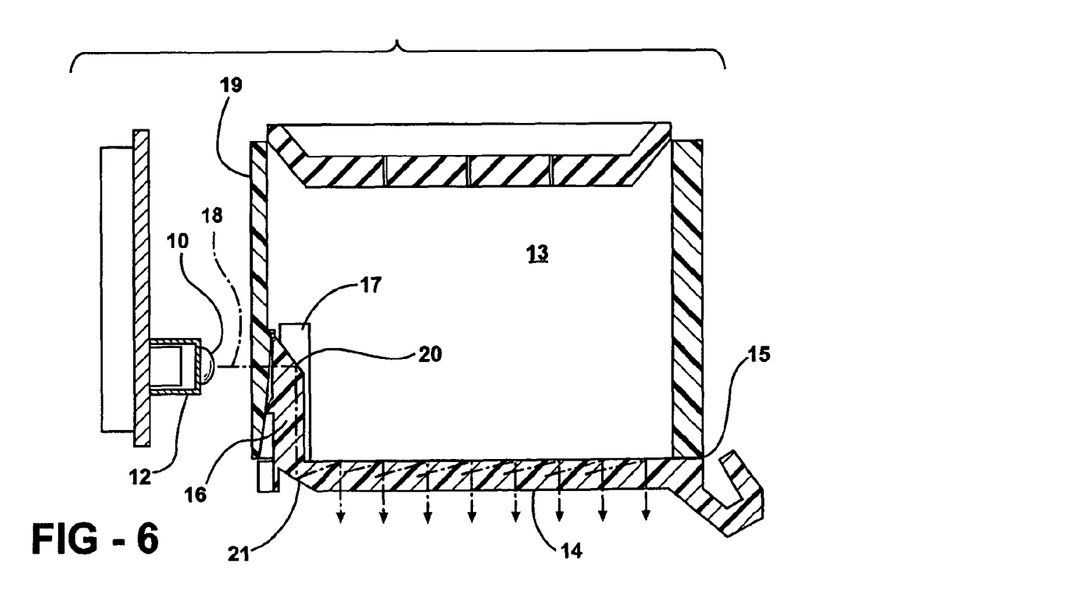
FIG. 6 is a cross-sectional view of one of the compartments of an electronic pillbox of the present invention which depicts how the LED's illuminate the cover of the compartment.

FIG. 5 is cross-sectional view of the electronic pillbox of FIG. 4 taken along sectional lines 5-5. FIG. 6 depicts some of the structural elements of the pillbox compartments. Each compartment 13 of the pillbox 1 has a cover 14 that can be opened. In the depicted embodiment, the cover 14 is pivotal about a hinge 15. In other embodiments, the cover 14 can be configured to slide between open and closed positions. The cover 14 is designed to receive light via a light pipe 16 and illuminate. In this regard, the cover 14 can be made of a light conducting and dispersing material and can additionally be physically configured, e.g. formed with lens or other optical structures, to receive and distribute light and illuminate.

In the embodiment depicted in FIG. 5 the light pipe 16 has a magnetic material 17 on at least one adjacent side. This magnet material 17 can be sensed by sensor 12 when sensor 12 is a magnetic sensor.

FIG. 6 is a cross-sectional view of one of the compartments of an electronic pillbox of the present invention which depicts how the LED's illuminate the cover of a compartment. As depicted in FIG. 6, light 18 from the LED 10 is directed though the side wall 19 of compartment 13 so that it impinges on a first reflective angled surface 20 of light pipe 16. The side wall 19 of the compartment 13 can be transparent for this purpose. Otherwise, an aperture or through-hole (not shown) can be provided in the side wall 19 of compartment 13 to allow light to pass therethrough. The light 18 is directed by first reflective angled surface 20 so that is impinges a second angled surface 21. The second angled surface 21 can be configured to disperse and direct the light though the cover 14 so as to illuminate cover 14. The side or surface of the cover 14 that closest to the interior of compartment 13 can be provided with a reflective coating or layer so as to direct light or illumination to the outer surface of the cover 14 as depicted. Whereas only LED 10 is depicted in FIG. 6, it is to be understood that the other LED's (including LED 11) are each positioned and aligned to direct a different color light toward light pipe 16 and thereby illuminate cover 14 when cover 14 is closed. A program within the circuit board can thus control the illumination of the LED's for example by a timing circuit so that the covers of selective compartments can be illuminated with a desired light color at the times when a medication within the compartments should be taken. As can be understood, a processor on the circuit board can control the illumination of the covers on individual compartment covers in a variety of manners. For example, a given color can be continuously illuminated with a given color at the time when a medication is to be take and can flash a given color after the time a medication was suppose to have been taken when the electronic pillbox confirms that the medication has not been taken. In addition, or alternatively to the illumination alert, the electronic pillbox can provide an audible alert, message, etc.

Figure 7:
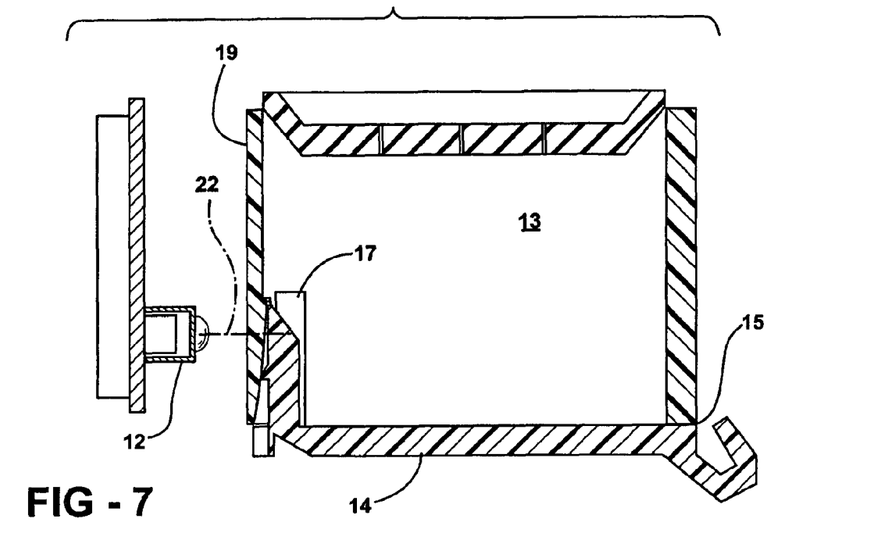
FIGS. 7 and 8 are cross-sectional views of one of the compartments of an electronic pillbox of the present invention which depict how the sensors 14 function to determine when the covers of the compartments have been opened.
Figure 8:
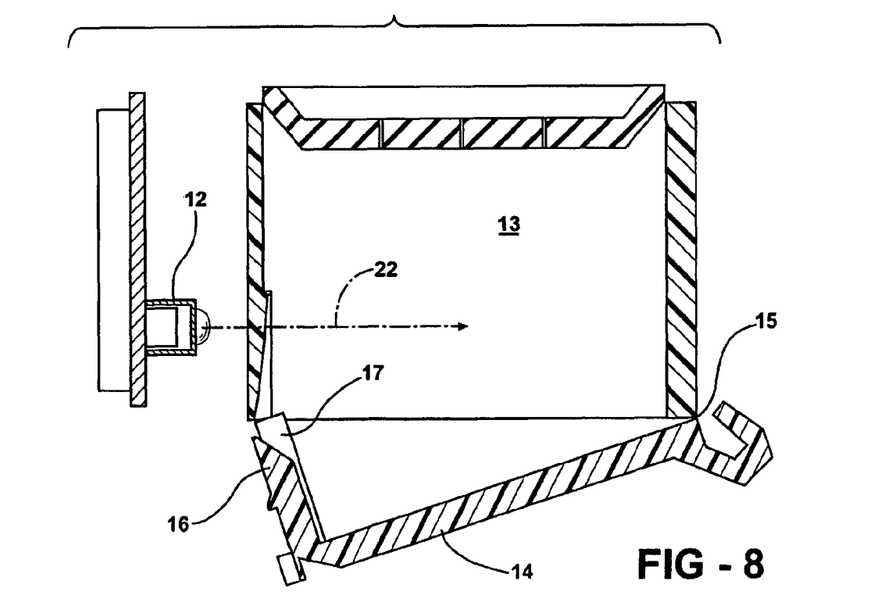

FIGS. 7 and 8 are cross-sectional views of one of the compartments of an electronic pillbox of the present invention which depict how the sensors 12 function to determine when the covers of the compartments have been opened. As depicted in FIGS. 7 and 8, radiation 22 from the sensor 12 is directed though the side wall 19 of compartment 13 so that it strikes light pipe 16. In the case where the cover 14 is closed as in FIG. 7, the radiation 22 or a portion thereof is reflected back after striking light pipe 16 and the reflected radiation 22 is detected by sensor 12. In the case where the cover 14 if opened as shown in FIG. 8, the radiation 22 does not reflect back toward sensor 12 so that the sensor 12 detects that the cover 14 is open.

By sensing or monitoring when a cover of a compartment has been opened, it can be determined or assumed that the medication within the compartment has been accessed and removed. Such removal of medication can further be determined or more reasonable assumed when the opening of a cover is correlated with illumination alerts of the cover of a compartment that signals a medication in a compartment should be taken (followed by confirmation that the cover of that compartment has been opened).

Figure 9:
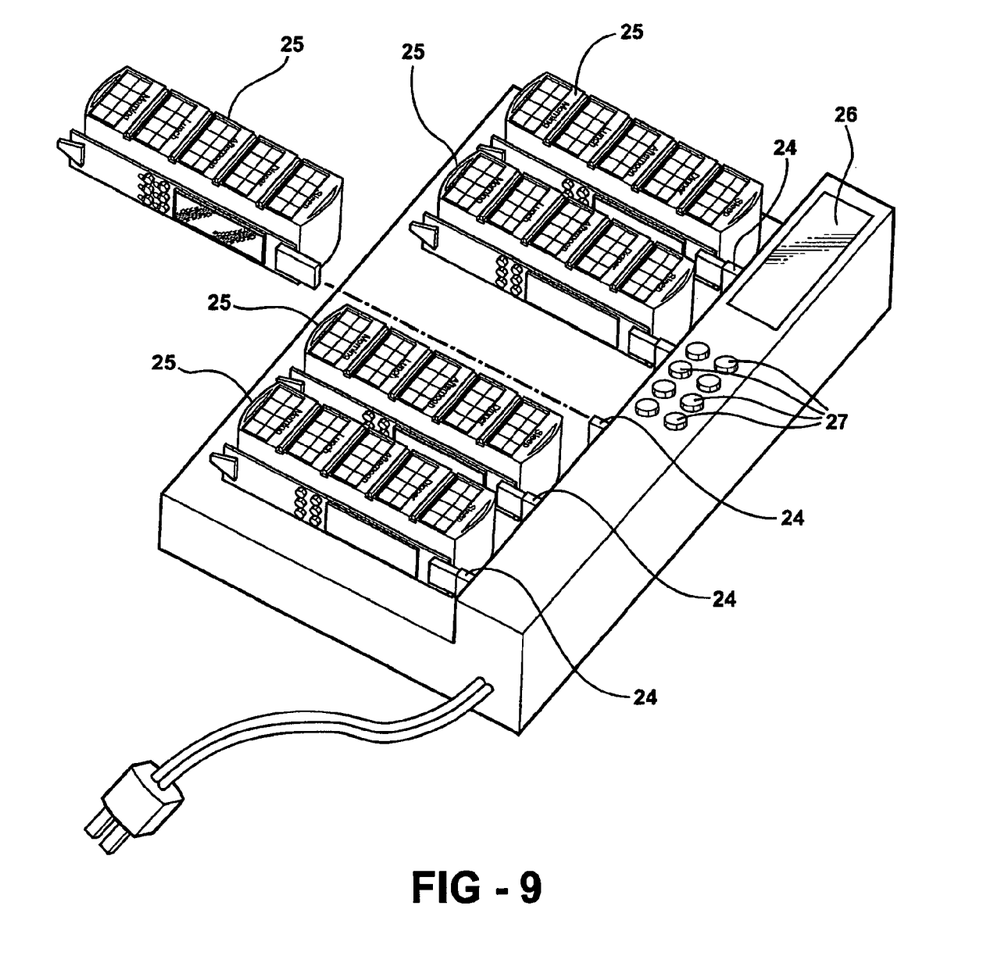
FIG. 9 is a perspective view of the electronic pillboxes positioned in a docking station according to one embodiment of the present invention.

FIG. 9 is a perspective view of the electronic pillboxes positioned in a docking station according to one embodiment of the present invention. The docking station 23 includes a plurality of USB connectors 24 which are arranged to be coupled to a plurality of electronic pillboxes 25. Alternatively, other type of connectors such as pin connectors could be utilized. Otherwise wireless connections can be provided. The docking station 23 includes a display 26 and either a plurality of buttons 27 or a control panel (not shown) which can be used to control the transfer of data between the individual electronic pillboxes 25 and the docking station 23 and the display of all data from either the docking station 23 and/or the individual electronic pillboxes 25. The docking station can be powered by a rechargeable or replaceable internal power supply and/or an electrical line that can be plugged into an external power supply.

The docking station can include a data transfer device such as a USB connection, pin connection, or wireless link and a programmable circuit to receive, transfer and correlate data between the electronic pillboxes 25 a computer, or mobile devices, including cell phones, pagers, interactive testing device, etc. directly or via the internet or cell phone transmission systems.

According to a further embodiment of the present invention, the circuit board can include a circuit that can covert spoken information into textual information. In this embodiment, a person, such as a healthcare professional, can speak the name of a particular medication and/or instructions into the microphone 4 and a program incorporated into the circuit board can translate the spoken information into textural or even graphic information and display the same on the displays of the electronic pillboxes or the display on the docking station. In addition the translated spoke information can be transferred as a data file to a computer, mobile device such as a cell phone which can store and/or display the textural or graphical information.

According to another embodiment of the present invention the circuit board, in addition to transferring various data files to a computer, mobile device, the electronic pillboxes of the present invention can send alerts to caregivers, family members, healthcare professionals, etc. that a patient has missed a dosage of medication has not been taken.

A further embodiment of the present invention will be discussed hereafter with reference to FIGS. 10-14, it being understood that features of interactive pillboxes that are discussed above can be incorporated in any combination into the pillboxes discussed in reference to FIGS. 10-14.

The embodiment of the invention shown in FIGS. 10-14 is based on a modular design that includes a platform or base unit to which can be coupled various modular components including electronic packages and different face or cover plates.

Figure 10:
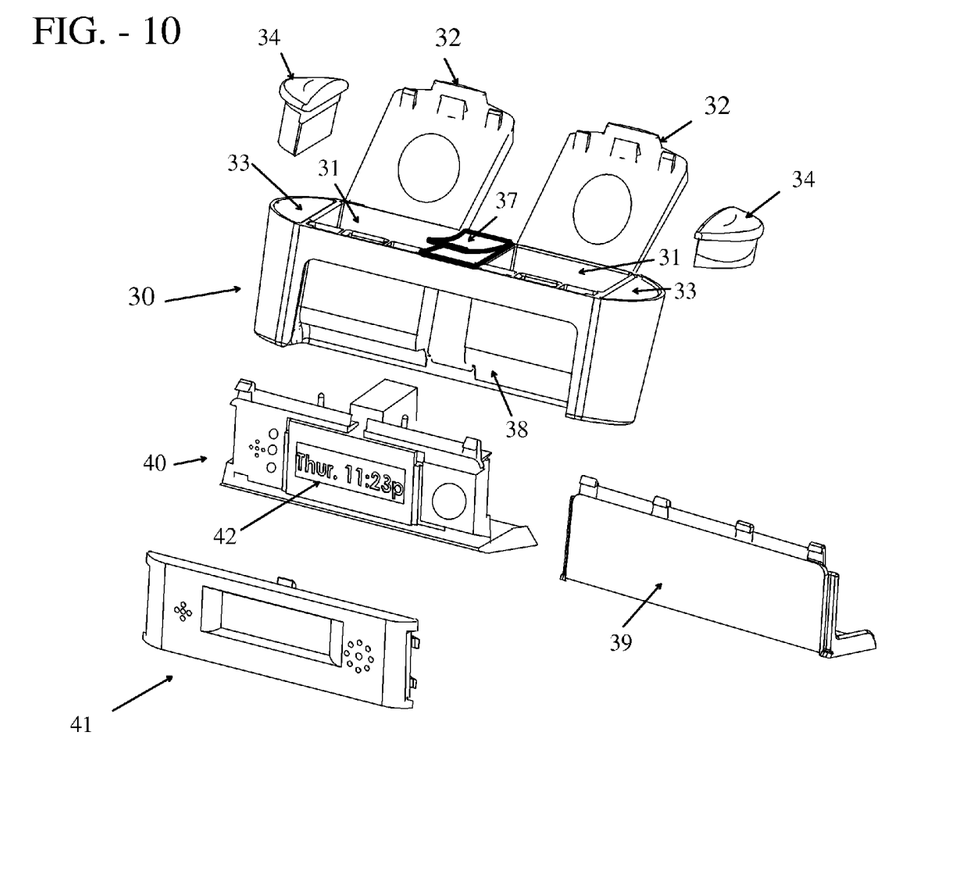
FIG. 10 is an exploded view of a modular pillbox according to one embodiment of the present invention.

FIG. 10 is an exploded view of a modular pillbox according to one embodiment of the present invention. As depicted in FIG. 10 the modular pillbox includes a platform or base unit 30 that is in the form of a multi-compartment unit with each compartment 31 having a door 32 through which access to the interior contents of the individual compartments can be gained. The doors 32 can include a latching mechanism that will secure the doors 32 in their closed positions and prevent accidental opening of the doors 32. The doors 32 can be provided with permanent or replaceable or interchangeable labels that indicate the time/day or other event when a user is suppose to access the contents of the compartments to take medications, vitamins, supplements, etc. stored in the compartments. The platform or base unit 30 can be made from any suitable material such as plastic materials, resin materials, metals, etc. and can be made by any convenient manner including, molding or machining all or part of the elements, assembling separate components or subcomponents of the platform or base unit 30 or any other suitable and conventional manufacturing processes. Further information where needed can be provided on the pillboxes in brail for those with impaired vision.

The platform or base unit includes channels 33 at either side which can be used to register the position of the platform or base with a docking station, storage unit, pill loading tray, etc. Although the channels 33 are show as have a half-circular shape, it is to be understood that in other embodiments they can have any desired shape. Both top caps 34 and bottom caps (not shown) are provided to close the tops and bottoms of channels 33. The top caps 34 and or bottom caps can be unique in color and/or structural appearance so as to individualize the pillboxes. In this manner two or more persons in a home or healthcare facility can use caps of different colors and/or structural appearances to identify their pillbox(es) from another person's.

At the backside of the platform or base unit 30 each of the compartments 31 is provided with the resilient, elastic, deflectable or flexible members disclosed in applicant's copending application Ser. No. 12/033,332 (the entire disclosure of which is hereby expressly incorporated by reference) that can comprise a flap that will yield to allow materials, pills or other articles can be passed therethrough. These flexible members, which will allow medicines, vitamins, supplements, etc. to be loaded into the compartments, 31 can be covered by their own covers (not shown) if desired. Such covers can be hinged or configured to slide open, be removable or have any desired configuration. In an alternative embodiment depicted in FIG. 11, resilient, elastic, deflectable or flexible members 35 disclosed in applicant's copending application Ser. No. 12/033,332 can be provided in the bottom of the platform or base unit 30 together with covers 36.

The platform or base unit 30 can include a clip 37 for securing the pillbox to a user's belt, garment waist band, purse strap, etc. In alternative embodiments the platform or base unit 30 can include a strap or hook or other means for carrying or coupling the pillbox to an article of clothing, purse strap, etc. A magnet can also be provided on the back of the platform or base unit and used to secure the pillbox to a metal surface such as a refrigerator door.

The front face of the platform or base unit 30 includes an opening 38 that is configured to receive various electronic packages or different face or cover plates.

FIG. 10 depicts a relatively plain face or cover plate 39 that does not include any electronic components. When face or cover plate 39 is coupled to the platform or base unit 30 over opening 38 the resulting pillbox is functional similar to the pillbox in applicant's copending application Ser. No. 12/033, 332. A pillbox that comprises the platform or base unit 30 and plain face or cover plate 39 and which is not provided with electronics can be offered to consumers as a basic pillbox which can be upgraded to have various electronic features, by merely replacing the plain face or cover plate 39 with an electronics package as discussed below. The plain face or cover plate can be printed with a day of the week identifier, a company logo or other advertisement or can have a label of such logo or advertisement placed thereon.

In an alternative embodiment the structural elements of the platform or base unit 30 that are exposed through opening 38 can be covered by an adhesive label rather than plain face or cover plate 39. Such a label can be printed with a day of the week identifier, a company logo or other advertisement or can have a label of such logo or advertisement placed thereon.

FIG. 10 depicts an electronics package 40 that can be received in the opening 38 and coupled to the platform or base unit 30. The electronics package 40 can provide a number of functions, including any or all of those that are discussed above in reference to FIGS. 1-9.

In FIG. 10, a removable/interchangeable face plate 41 for the electronics package 40 is depicted. According to one embodiment the face plate 41 is provided with a set of pins or pegs (e.g., three) that extend out from the back to contact switches on the electronic package. The pins can be selectively removed so that a combination of the remaining pins will engage a combination of the switches of the electronics package 40. In this manner a commonly fabricated face plate 41 can modified to engage a desired combinations of the switches on the electronics package 40 thereby setting the day of the week for individual pillboxes.

The electronics package 40 can include a timer that displays current date and time information on display 42. In addition to displaying the data and time the display 42 can be used to display any desired information, instructions, graphics, etc. such as emergency contact information, drug allergies, user identification, etc. The timer can be used to activate an alarm that will signal when a particular medicine, vitamin, supplement, etc. should be taken or if a doctor's appointment, medial test, etc. is immediately scheduled. In such an instance the alarm can be an audible alarm (via a speaker), visual alarm (via one or more light sources, e.g. LED's), mechanical alarm (including vibrating mechanism) or any combination thereof. The timer can also be used in conjunction with a microprocessor to keep track of when individual doors 32 of the compartments 31 are opened, closed and the duration of the doors 32 being opened as a way to determine when a particular medicine, vitamin, supplement, etc. has been taken. Further the timer could be used to operate a latch release mechanism that will allow a user to open a particular compartment door 32 at a given time. In this regard the electronics package 40 can include electro-mechanical elements such as movable latching mechanisms, sensors for sensing when the doors 32 are opened, etc. that extend into the platform or base unit 30 to be aligned and position to affect latching (and release) of the compartment doors 32, sensing opening of the compartment doors 32, etc. Further the electronics package can include electro-optical elements that LED's and light pipes that cooperate with the platform or base unit 30 to illuminate doors 32 as discussed above in reference to the embodiments of the invention discussed in reference to FIGS. 1-9 and further elements that affect the various functions of the invention as discussed above.

In another embodiment the electronics package 40 can include a speaker and microphone for playing and recording messages. In such an embodiment the electronics package 40 can be provided with a conventional miniaturized recording device with any suitable switches for activating recording and playing functions. Pre-recorded or pre-stored messages could also be provided and selected by an onboard software application that monitors usage and function of the pillbox.

Examples of messages that can be recorded and played include audio reminders to take medicines, vitamins, supplements, etc. at proper times and/or instructions particular to certain medicines, vitamins, supplements, etc. such as "take with food." In addition a recording could play which asks the user for feedback, such as rating pain, noting hours slept, recording temperature, appetite, etc. (all tagged with date/time information from the timer) to which auto prompts the user could enter responses by means of a touch switch by which consecutive repeated touches registers an increased numeric value, a touch sensitive mouse switch of the type provided on cell phones, a touch slide panel switch, a number pad, etc. In this regard, the display shown in FIG. 10 can visually verify entered response values (as well as alternatively solicit such responses). Such recorded responses together with any audio recorded response messages can be stored in a memory chip and presented to a physician, medical assistant, caregiver, family member, etc. on presentation of the pillbox or after being obtained by transmitted via wireless transmission through a Wi-Fi or similar wireless connection or over a telephone connection to a physician, medical assistant, caregiver, family member. In further embodiments of the present invention recorded responses, symptom input such as pain rating, hours slept, temperature, appetite, dizziness, etc. can be transmitted via wireless transmission through a Wi-Fi or similar wireless connection or over a telephone or direct connection to a computer that is used for monitoring and managing a subject's healthcare and maintain a medical healthcare journal.

Figure 11:
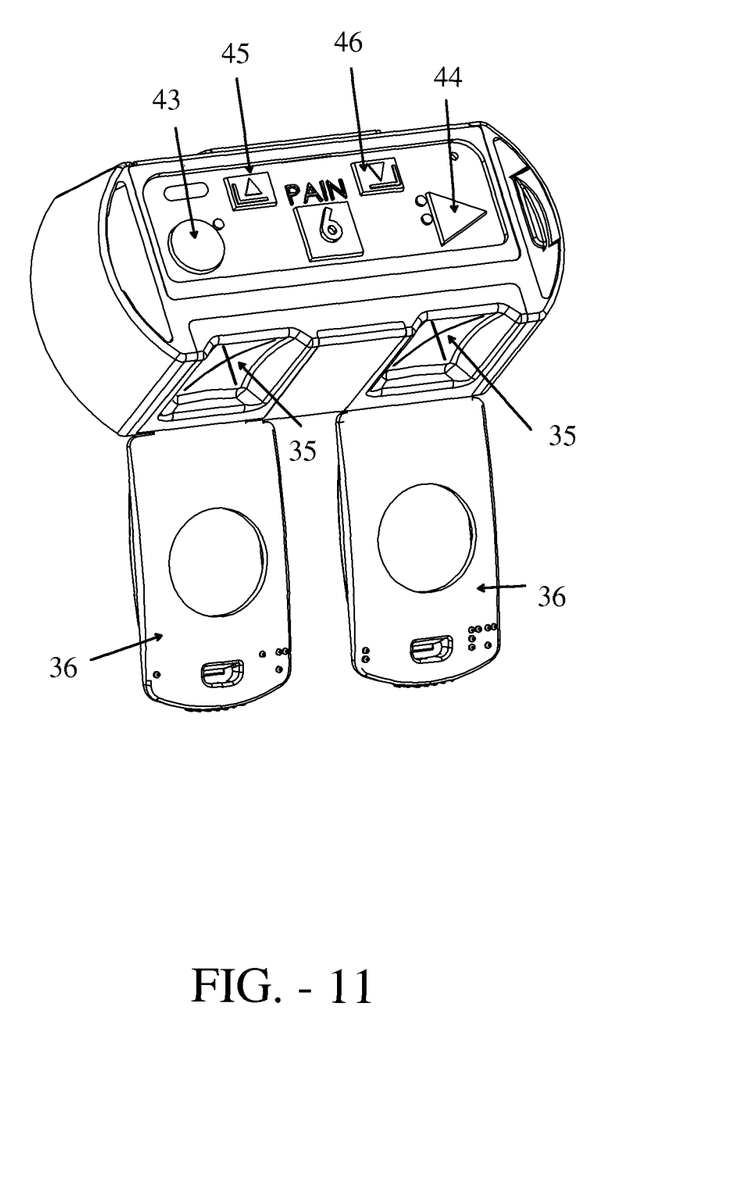
FIG. 11 is a perspective view of an electronic pillbox according to one embodiment of the present invention.

FIG. 11 is a perspective view of an electronic pillbox according to one embodiment of the present invention. The electronic pillbox of FIG. 11 includes the platform or base unit 30 of FIG. 10 and an electronics package 40. The electronics package 40 show in FIG. 11 includes a recording switch 43 and a play switch 44 and a display on which a user can enter and verify a level of pain (or other symptom) that is being experienced using buttons 45 and 46. The electronics pillbox of FIG. 11 includes the resilient, elastic, deflectable or flexible members 35 disclosed in applicant's copending application Ser. No. 12/033,332 in the bottom of the platform or base unit 30 together with covers 36 as noted above. The electronic pillbox can have a touch screen that can be used to both display information and to enter responses. In the case of a numerically rated response such as pain rating a voice active or voice recognition input circuit can be included. Alternatively graphic displays could be presented which as a smiley face for little or no pain, a non-smiling face for moderate pain and a crying face for more severe pain could be displayed and selected, it being understood that these graphical examples are non-limiting.

Figure 12:
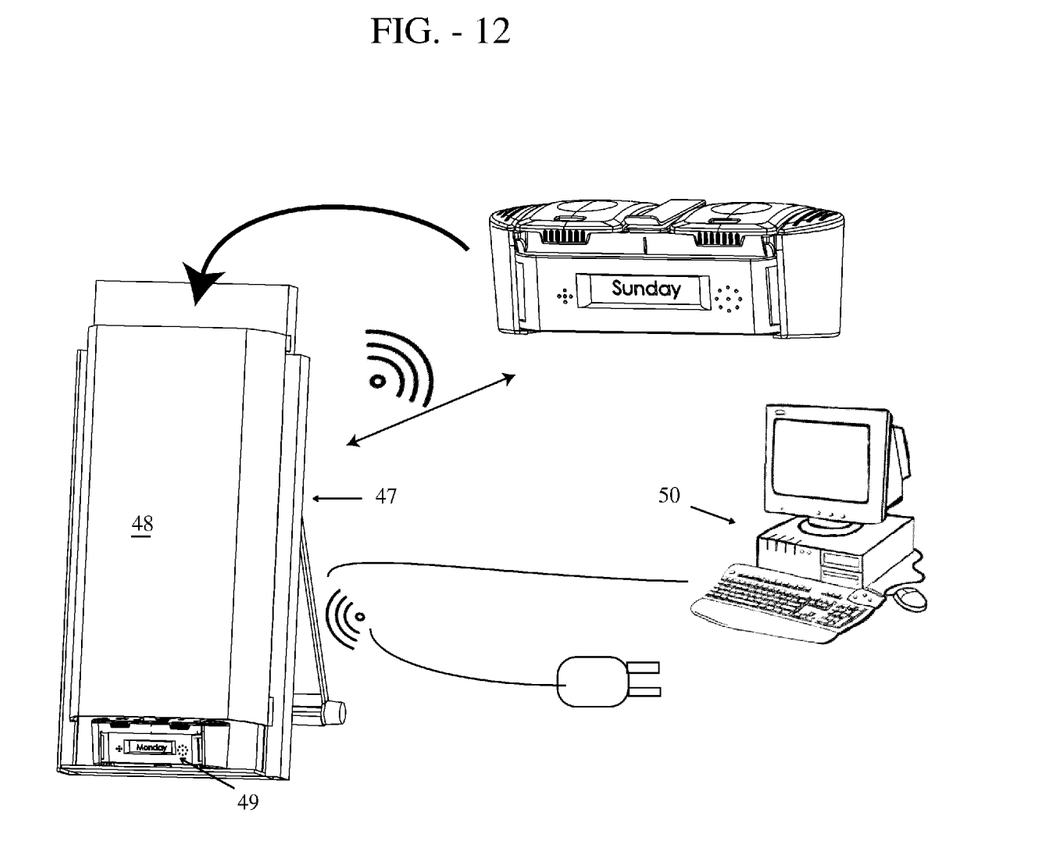
FIG. 12 is a depiction of a storage magazine for the pillboxes of the present that illustrates how the electronic pillboxes interact with a computer.

FIG. 12 is a depiction of a storage magazine for the pillboxes of the present that illustrates how the electronic pillboxes interact with a computer. The storage magazine 47 is configured to allow individual pillboxes to be dropped into the top of the storage magazine 47 and held therein so that only the lower most pillbox 49 can be removed at the bottom. In this regard at least the sides of the storage magazine extend around the sides of the pillboxes so as to prevent the pillboxes from being removed from the storage magazine 47 except at the bottom where the sides of the storage magazine 47 do not extend around the side of the pillboxes. Alternatively as depicted in FIG. 12, the storage magazine 47 includes a closed front 48 that is only opened at the bottom. In a further embodiment the bottom of the storage magazine 47 can include a cover that can be opened to access and removed the lower most pillbox 49. In a further embodiment the storage magazine 47 can include a release mechanism that releases the lower most pillbox 49 when the last pillbox in a set is placed in the top of the storage magazine 47.

The pillboxes are dropped into the top of the storage magazine 47 and fall downward under the influence of gravity. In the case of pillboxes that are not provided with electronics, the storage magazine 47 can be used to present (at the bottom) the next pillbox a user needs to carry, such as Monday's pillbox after refilling and placing Sunday's pillbox in the top of the storage magazine 47.

In the case of electronic pillboxes, the pillboxes can get programmed and transmit information wirelessly when they are placed in the storage magazine. As indicated the electronic pillboxes can transmit and receive information wirelessly between the storage magazine 47 and a computer 50. The transmitted information can include the dates/times medication, vitamins, supplements, etc, were taken, as well information entered into the electronic pillboxes such as symptom information such as pain rating, hours slept, temperature, appetite, dizziness, etc. recorded messages (all tagged with date/time information from the timer). Received or program information can include adjustments as to when to take medicines, vitamins, supplements, etc., dosage amounts, additional medicines, discontinue medicines, vitamins, supplements, etc. to take, reminders of doctor appointments, etc. The transmitted and received information can be relayed via the internet to the user's healthcare provider who can monitor and adjust the user's medicines, vitamins, supplements, etc. The transmitted and received information can also be sent to a computer (or computer network) that is used for monitoring and managing a subject's healthcare and maintain a medical healthcare journal.

In other embodiments of the invention the electronic pillboxes themselves could wirelessly communicate to the user's healthcare provider through the internet. In such an embodiment (and in the embodiments above) each electronic pillbox would include a unique identification code that would be verified before transmitting and receiving data.

In the case of electronic pillboxes the onboard power supplies of the electronic pillboxes could be charged while the electronic pillboxes are in the storage magazine 47. Alternatively the onboard power supplies of the electronic pillboxes could be charged via a plug in power cord or through inductive wireless charging which can be incorporated into the storage magazine 47 or a charging pad or station.

Figure 13:
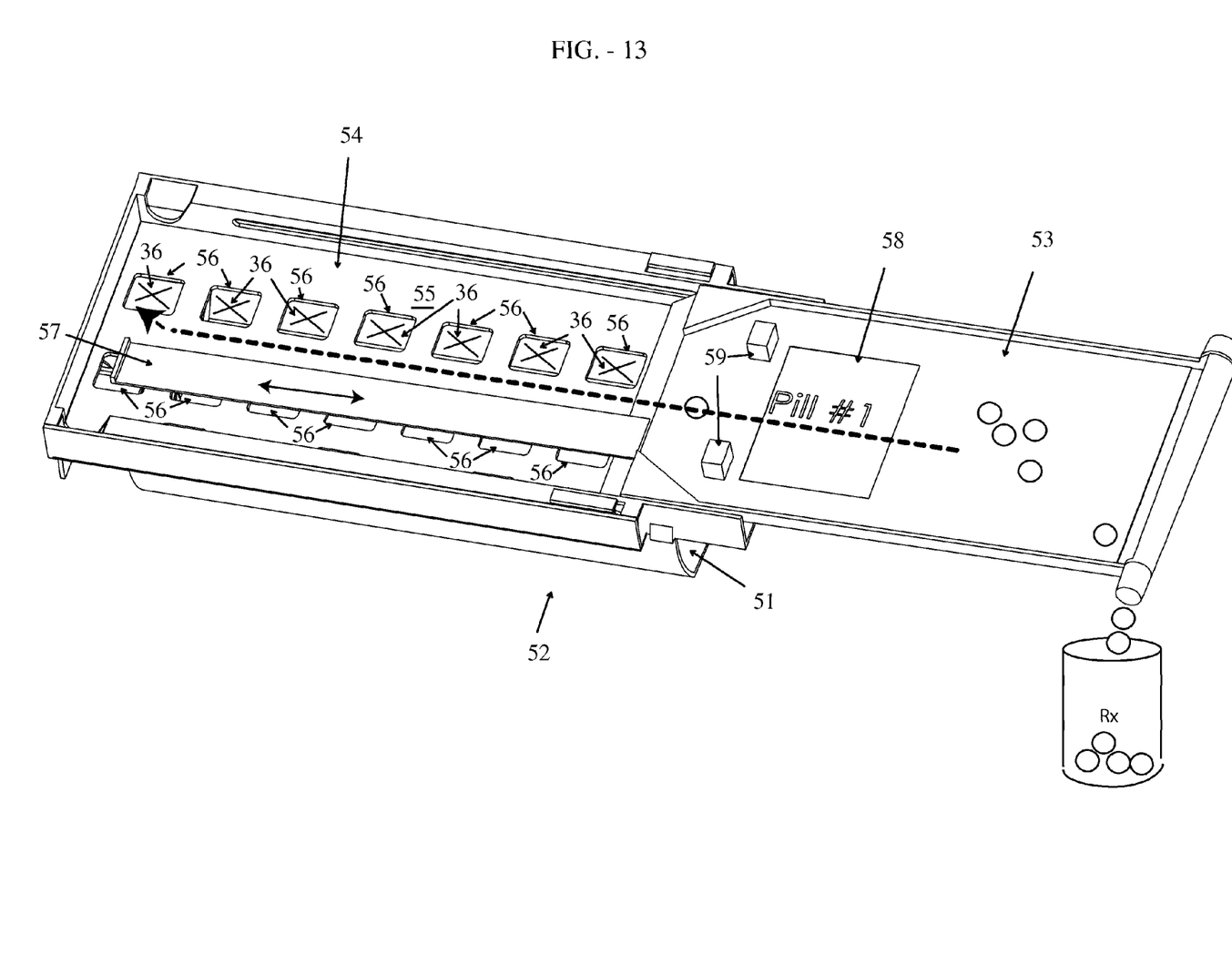
FIG. 13 depicts how medicines, vitamins, supplements, etc. are loaded into the pillboxes according to one embodiment of the present invention.

FIG. 13 depicts how medicines, vitamins, supplements, etc. are loaded into the pillboxes according to one embodiment of the present invention. To load medicines, vitamins, supplements, etc. into the pillboxes, a plurality of pillboxes having the resilient, elastic, deflectable or flexible members 35 in the bottoms of the platforms or base units 30 can be arranged as shown in FIGS. 31 and 32 of applicant's copending application Ser. No. 12/033,332 and medicines, vitamins, supplements, etc. can be loaded as discussed in applicant's copending application. In embodiments in which the resilient, elastic, deflectable or flexible members 36 are in the back sides of the platforms or base units 30 can be received in opposed complementarily shaped channels 51 in the loading tray 52 shown in FIG. 13. The loading tray 52 shown in FIG. 13 includes a pill sorting area 53 in which a number of pills can be deposited, and a pill loading area 54. Reference herein to "pill" or "pills" is intended to include and encompass tablets, capsules, gel caps, gummy gels and other types and/or carriers of medicines, vitamins and health supplements. The pill loading area 54 includes a panel 55 having openings 56 therein which align and register with the resilient, elastic, deflectable or flexible members 36 of the underlying pillboxes. If desired, blocking members 57 (one shown) can be positioned across openings 56 in panel 55 to prevent pills from being inadvertently loaded into compartments of the underlying pillboxes. The blocking members 57 can be pulled out from the base of the pill sorting area 53 which itself can be pivotally coupled to the pill loading area 54 so as to allow the loading tray 52 to be folded into a compact shape.

In order to ensure accurate loading of pillboxes the containers of the medicines, vitamins, supplements, etc. have readable data such as a barcode, magnetic strip, etc. This data can be read and confirmed by a compatible reader provided on the loading tray or otherwise read and confirmed by an auxiliary reader. Likewise each pillbox can be provided with readable data such as a barcode, magnetic strip, etc. which can be read and confirmed so as to positively match the containers of the medicines, vitamins, supplements, etc. with the correct set of pillboxes.

The sorting area 53 of the loading tray 52 can be provided with a display 58 and a pair of sensor elements 59 that count and display the number of pills that have been loaded. In this regard, the path that the pills are slide is indicated by the broken line arrow which passes between the pair of sensor elements 59, one of which can transmit radiation to be received by the other unless the path between them is interrupted.

Figure 14:
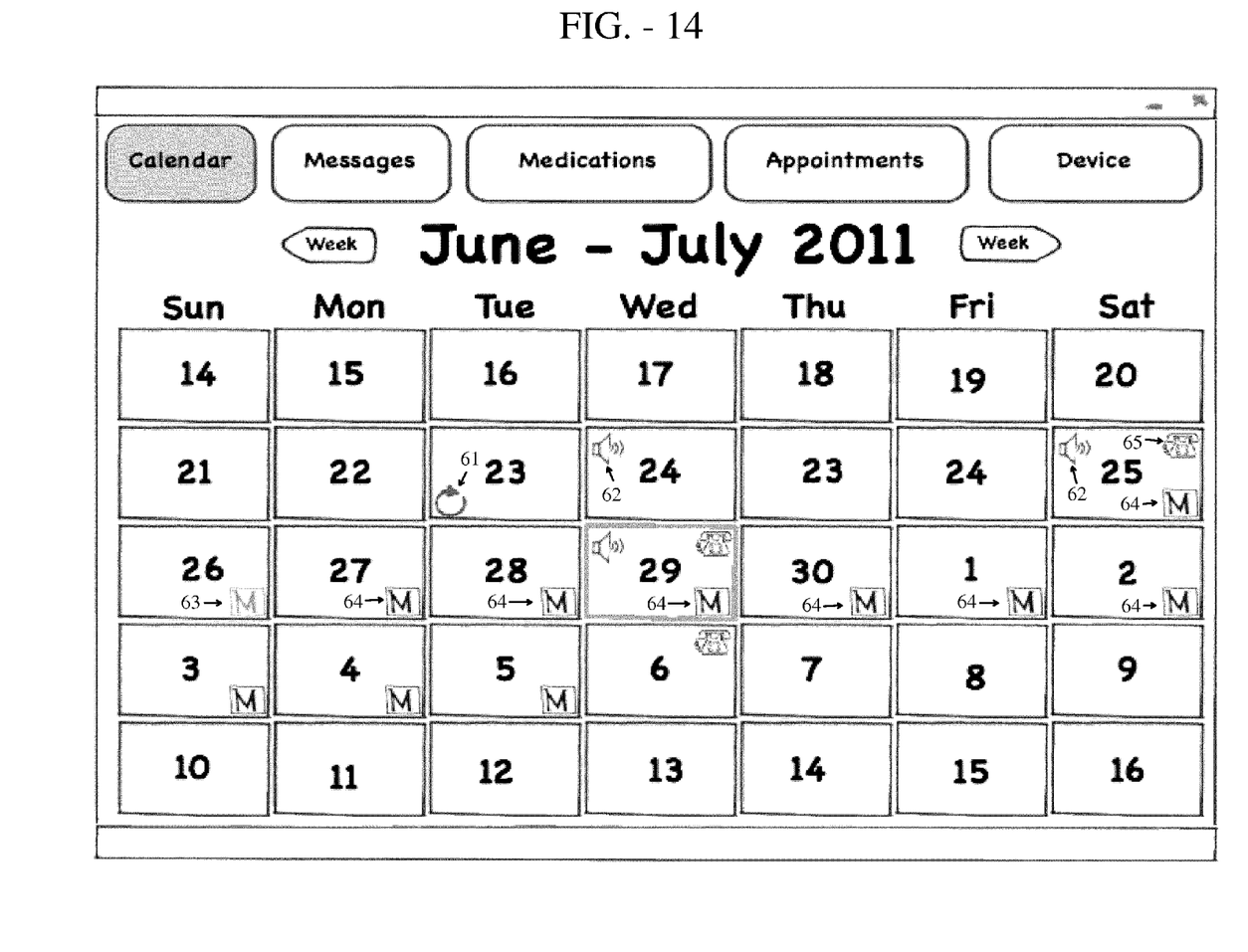
FIG. 14 illustrates how the interactive pillboxes of the present invention allow for management of healthcare.

FIG. 14 illustrates how the interactive pillboxes of the present invention allow for management of healthcare. FIG. 14 is a non-limiting example of the main page of a computer software program that can be used to manage the healthcare of a person using the electronic pillboxes of the present invention. FIG. 14 depicts a calendar showing the days of the week for a desired number of days. Icons depicted on certain days include an icon 61 which indicates when a user's pillboxes were synchronized with the computer program, i.e. when information noted above was transferred between the pillboxes and computer. Icon 62 indicates when a recorded message is scheduled to be played to the user of the pillboxes. Icon 63 indicates when a user failed to take a medication that was scheduled for that day of the week that the icon 63 is shown on. Icons 64 indicate when a medication is scheduled to be taken, it being noted that icons 62 and 63 can be of a different color to distinguish the two, or icon 62 can flash or otherwise look different from icon 63. Icon 65 indicates when a medical appoint has been scheduled.

At the top of FIG. 14 are links to other pages including a "Messages" link that provides a page from which messages can be recorded and sent to a user's pillboxes and/or retrieved from a user's pillboxes and listened to. Also shown is a "Medications" link that provides a page that will allow a healthcare to schedule which medications to take, including the dosages and when to take such medications. This information will be relayed to the user or an attendant who loads future medications into pillboxes.

Also shown is an "Appointments" link that will allow a healthcare provider to schedule office or home visits with a user. The "Device" link will provide a page from which a healthcare provider can manage the synchronization of a user's pillboxes, including verification of transferred information and general system maintenance tools. FIG. 14 is merely a non-limiting example that is provided to discuss how the pillboxes of the present invention allow for remote monitoring and managing of a person's healthcare and maintaining medical journals.

As an example of the type of interactivity that the present invention provides a person can voluntarily, or after receiving a prompt, input pain level or rating information into an electronic pillbox. That information can then be transferred to a medical care provider who, can consider the user's pain level or rating in conjunction with medication type and dosage and can change the medication or dosage in a subsequent week or date.

To assist and encourage a healthy lifestyle the pillboxes of the present invention can be provided with the components and function of a pedometer.

Although the present invention has been described with reference to particular means, materials and embodiments, from the foregoing description, one skilled in the art can easily ascertain the essential characteristics of the present invention and various changes and modifications can be made to adapt the various uses and characteristics without departing from the spirit and scope of the present invention as described above and as set forth in the attached claims.

What is claimed is:

1. A modular pillbox which comprises a base unit and a plurality of modules that can be interchangeably coupled to the base unit,
   the base unit comprises:
      a plurality of interior compartments defined by a top, a bottom and at least one side wall;
      openable doors that close the tops of the plurality of interior compartments;
      one-way passages in one of the bottoms or the at least one side wall of each interior compartment through which pills can be pushed into the interior compartments; and
      an opening in a front portion of the base unit,
   the plurality of modules comprise:
      a cover plate that couples to the base unit and covers the opening; and
      an electronic package that couples to the base unit and covers the opening.

2. A modular pillbox according to claim 1, wherein the electronic package comprises a microphone and a speaker for recording and playing messages.

3. A modular pillbox according to claim 1, wherein the electronics package comprises a timer and an alarm which is activated by the timer.

4. A modular pillbox according to claim 3, wherein the alarm comprises at least one of an audible alarm, a visual alarm and a mechanical alarm.

5. A modular pillbox according to claim 1, wherein the electronics package comprises means for sensing when doors of the plurality of compartments have been opened.

6. A modular pillbox according to claim 1, wherein the electronics package comprises a data transfer device for transferring data between the pillbox and an auxiliary device.

7. A modular pillbox according to claim 1, wherein the electronics package includes a program for converting spoken information into data that can be displayed as an image or transmitted.

8. A modular pillbox according to claim 1, in combination with a storage magazine which storage magazine is configured to receive a plurality of said modular pillboxes and transfer data between said plurality of modular pillboxes and a remote terminal.

9. A modular pillbox according to claim 1, in combination with a loading tray for loading pills in the compartments of a plurality of the modular pillboxes, the loading tray being configured to couple to a plurality of the modular pillboxes so as to present all of the one-way passages in an array so that pills can be pushed through selected ones of the one-way passages.

10. An electronic interactive pillbox which comprises a base unit and a replaceable electronics module that can be removable coupled to the base unit,
the base unit comprises:
  a plurality of interior compartments defined by a top, a bottom and at least one side wall;
  openable doors that close the tops of the plurality of interior compartments;
  one-way passages in one of the bottoms or the at least one side wall of each interior compartment through which pills can be pushed into the interior compartments; and
  an opening in a front portion of the base unit,
the electronics module comprises:
  an electronic package that removably couples to the base unit within the opening so that close the opening and define a front face of the resulting electronic interactive pillbox,
  the electronic package coupling the electronic interactive pillbox to a remote terminal at which a healthcare provider can monitor, manage, evaluate and maintain a periodic record of the healthcare of a user of the electronic interactive pillbox.

11. An electronic interactive pillbox according to claim 10, wherein the electronic package comprises a microphone and a speaker for recording and playing messages.

12. An electronic interactive pillbox according to claim 10, wherein the electronics package comprises a timer and an alarm which is activated by the timer.

13. An electronic interactive pillbox according to claim 12, wherein the alarm comprises at least one of an audible alarm, a visual alarm and a mechanical alarm.

14. An electronic interactive pillbox according to claim 10, wherein the electronics package comprises means for sensing when doors of the plurality of compartments have been opened.

15. An electronic interactive pillbox according to claim 10, wherein the electronics package comprises a data transfer device for transferring data between the pillbox and the remote terminal.

16. An electronic interactive pillbox according to claim 10, wherein the electronics package includes a program for converting spoken information into data that can be displayed as an image and/or transmitted.

17. electronic interactive pillbox according to claim 10, wherein the electronic package receives symptom input information from a user and transfers the inputted symptom information to the remote terminal to allow the healthcare provider to monitor symptom information.

18. An electronic interactive pillbox according to claim 10, in combination with a storage magazine which storage magazine is configured to receive a plurality of said electronic interactive pillboxes and transfer data between said plurality of electronic interactive pillboxes and a remote terminal.

19. An electronic interactive pillbox according to claim 10, in combination with a loading tray for loading pills in the compartments of a plurality of the electronic interactive pillboxes, the loading tray being configured to couple to a plurality of the electronic interactive pillboxes so as to present all of the one-way passages in an array so that pills can be pushed through selected ones of the one-way passages.

20. An electronic interactive pillbox according to claim 15, wherein the electronics package transmits information wirelessly or via a wired connection to either one of a computer terminal or telephone.

* * * * *